(12) United States Patent
Niccolai

(10) Patent No.: US 6,705,313 B2
(45) Date of Patent: Mar. 16, 2004

(54) DEVICE USABLE IN THE TREATMENT OF AFFECTIONS OF THE AIRWAYS

(75) Inventor: Fabrizio Niccolai, Milan (IT)

(73) Assignee: PH&T S.p.A., Milan (IT)

( * ) Notice: Subject to any disclaimer, the term of this patent is extended or adjusted under 35 U.S.C. 154(b) by 0 days.

(21) Appl. No.: 10/141,142

(22) Filed: May 9, 2002

(65) Prior Publication Data
US 2003/0131847 A1 Jul. 17, 2003

(30) Foreign Application Priority Data
Jan. 16, 2002 (IT) .................................. MI2002A0078

(51) Int. Cl.$^7$ ............................................. A61M 13/00
(52) U.S. Cl. .............................. 128/203.21; 128/203.15
(58) Field of Search ...................... 128/203.15, 203.21; 604/58

(56) References Cited

U.S. PATENT DOCUMENTS

| | | | | | |
|---|---|---|---|---|---|
| 2,517,482 A | * | 8/1950 | Hall | ................ | 128/203.15 |
| 3,507,277 A | * | 4/1970 | Altounyan et al. | ..... | 128/203.15 |
| 3,518,992 A | * | 7/1970 | Altounyan et al. | ..... | 128/203.21 |
| 3,837,341 A | * | 9/1974 | Bell | ................ | 128/203.15 |
| 3,888,253 A | * | 6/1975 | Watt et al. | .............. | 128/203.15 |
| 3,906,950 A | * | 9/1975 | Cocozza | ................ | 128/203.15 |
| 3,918,451 A | * | 11/1975 | Steil | ................ | 128/203.21 |
| 3,949,751 A | * | 4/1976 | Birch et al. | .............. | 128/203.15 |
| 3,971,377 A | * | 7/1976 | Damani | ................ | 128/200.17 |
| 3,991,761 A | * | 11/1976 | Cocozza | ................ | 128/203.15 |
| 4,069,819 A | | 1/1978 | Valentini et al. | ........ | 128/203.15 |
| 4,116,195 A | * | 9/1978 | James | ................ | 604/244 |
| 4,884,565 A | * | 12/1989 | Cocozza | ................ | 128/203.21 |
| 4,889,114 A | | 12/1989 | Kladders | ................ | 128/203.15 |
| 4,995,385 A | * | 2/1991 | Valentini et al. | ........ | 128/203.21 |
| 5,048,514 A | * | 9/1991 | Ramella | ................ | 128/203.21 |
| 5,372,128 A | * | 12/1994 | Haber et al. | ........... | 128/203.21 |
| 5,522,383 A | * | 6/1996 | Calvert et al. | ......... | 128/203.15 |
| 5,619,985 A | * | 4/1997 | Ohki et al. | ............. | 128/203.21 |
| 5,647,349 A | * | 7/1997 | Ohki et al. | ............. | 128/203.15 |
| 5,685,294 A | * | 11/1997 | Gupte et al. | ............ | 128/203.15 |
| 5,715,811 A | * | 2/1998 | Ohki et al. | ............. | 128/203.21 |
| 5,752,505 A | * | 5/1998 | Ohki et al. | ............. | 128/203.15 |
| 5,810,004 A | * | 9/1998 | Ohki et al. | ............. | 128/203.15 |
| 5,921,236 A | * | 7/1999 | Ohki et al. | ............. | 128/203.15 |
| 6,092,522 A | * | 7/2000 | Calvert et al. | ......... | 128/203.21 |
| 6,273,086 B1 | * | 8/2001 | Ohki et al. | ............. | 128/203.21 |
| 6,298,846 B1 | * | 10/2001 | Ohki et al. | ............. | 128/203.15 |
| 6,341,605 B1 | * | 1/2002 | Ohki et al. | ............. | 128/203.15 |

FOREIGN PATENT DOCUMENTS

| | | |
|---|---|---|
| EP | 0 385 156 | 9/1990 |
| EP | 0 388 621 | 9/1990 |

* cited by examiner

Primary Examiner—Aaron J. Lewis
(74) Attorney, Agent, or Firm—Oblon, Spivak, McClelland, Maier & Neustadt, P.C.

(57) ABSTRACT

A device defining a chamber for housing a capsule containing a product in fine powder form, comprising a manually movable part provided with needles which perforate the capsule when the movable part is operated and leave the capsule when the movable part is released, the entire product in powder form escaping from the capsule, to be inhaled.

5 Claims, 1 Drawing Sheet

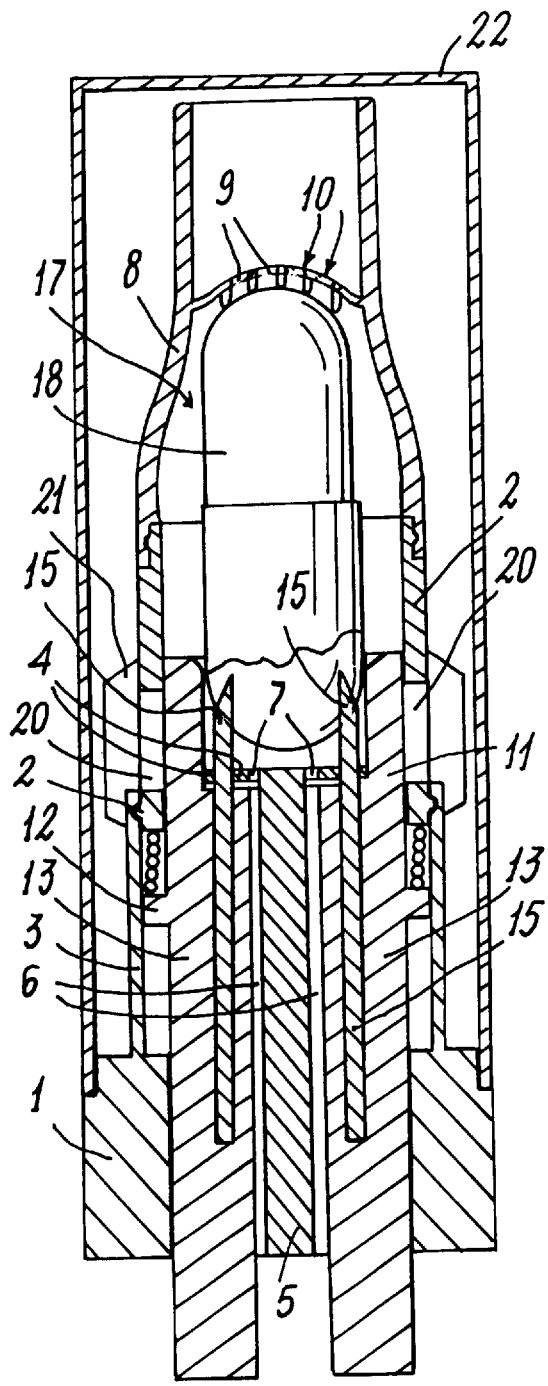
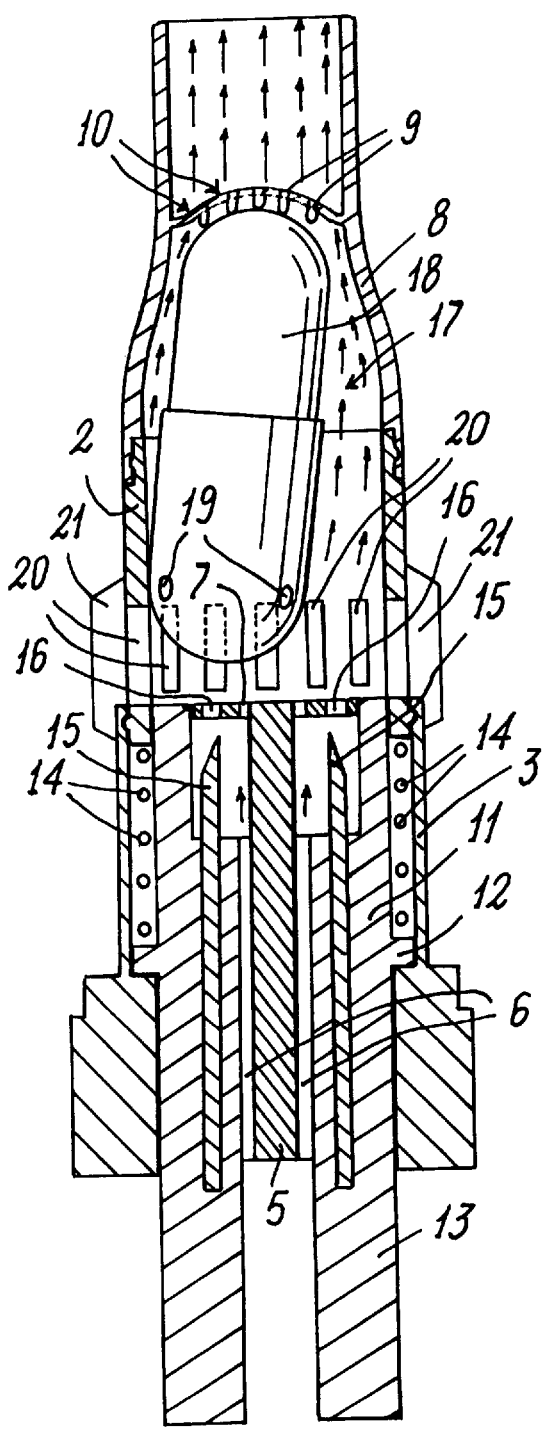
FIG. 1
FIG. 2

DEVICE USABLE IN THE TREATMENT OF AFFECTIONS OF THE AIRWAYS

BACKGROUND OF THE INVENTION

1. Field of the Invention

The present invention relates to an inhaler which enables its user to inhale fine powders contained in capsules.

2. State of the Art

Many products such as peptides, antihistamines, many types of antibiotics and pharmaceutical substances, herbal, antioxidant and similar substances) are known to be used in the form of fine powders enclosed in capsules generally of elongate form. These products are inhaled by the user using a device (commonly called an inhaler) defining a chamber in which a capsule is housed, to be perforated or broken within this chamber and allow the powder product to escape and be inhaled by the user via a mouthpiece or the like. Various types of inhaler are known, such as those illustrated in U.S. Pat. No. 4,069,819 and in particular in U.S. Pat. No. 4,995,385 and in the corresponding European Patent No. 0 388 621 A1 to which specific reference will be made hereinafter as state of the art.

The inhaler illustrated in U.S. Pat. No. 4,995,385 and EP-B-0388621 has a capsule housing chamber bounded by a main body and by a movable part provided with thin needles or the like which perforate the capsule when the movable part is moved towards and against the capsule. When the movable part is withdrawn, the product in fine powder form contained in the capsule is able to escape through the holes made in it by the needles, its escape being facilitated by the fact that the capsule has dimensions less than those of the chamber in which it is housed, and the fact that in the inhaler, in the lower lateral part of the chamber, there are provided a plurality of windows or apertures with their axis inclined to the axis of the inhaler, in order to transmit to the capsule a rotary movement within the chamber when the user inhales air through the inhaler.

The upper part of the chamber is bounded by a profiled wall comprising a plurality of small holes through which the air inhaled through the inhaler mouthpiece passes, entraining with it the powder which has escaped from the capsule.

The drawback of the aforedescribed inhaler (and of all known inhalers) is the fact that a part of the powder product which has escaped from the capsule deposits on the base of the chamber and about the needles which have perforated the capsule. In this respect, when the inhaler is used, it is held in a substantially vertical position, and the air which is drawn into the chamber through the apertures is unable to remove a part of the powder deposited on the base of the chamber and mix it with the air drawn in.

SUMMARY OF THE INVENTION

The main object of the present invention is to provide an inhaler of the aforestated type able to prevent the product in powder form from depositing and collecting on the base of the chamber housing the capsule, such that the entire product in powder form which escapes from the capsule is mixed with the air drawn in by the user.

Another object is to provide an inhaler which is of easy use, of simple structure and of low production cost.

These and further objects are attained by an inhaler for inhaling fine powder contained in capsules of substantially cylindrical shape, comprising an elongate main body, a top part applied to the upper end of the main body and defining therewith a chamber for housing a capsule containing a fine powder to be inhaled, and a movable part guided on the main body and having a portion which projects lowerly from the main body and a portion which has at least one pointed rod extending towards said chamber, the movable part being translatable between an inactive position in which the pointed end of the rod is outside said chamber and an active position in which said end of the rod extends into the chamber in order to perforate a capsule housed therein, in the lower part of the chamber there being provided a plurality of apertures which open to the outside of the peripheral lateral surface of the inhaler, the upper part of the chamber being bounded by a wall which is traversed by a plurality of small holes and is rigid with the top part, the dimensions of the chamber being greater than those of the capsule which it is intended to house, characterised by presenting at least one longitudinal hole which opens at the lower part of said chamber and, respectively, at the lower portion of the movable part to enable air to flow into the chamber from below.

BRIEF DESCRIPTION OF THE DRAWINGS

Preferably, said longitudinal hole is rectilinear and is parallel to the axis of translation of the movable part between its inactive and active positions, between the main body and the movable part there acting at least one spring which urges the movable part towards its inactive position.

Again preferably, the chamber for housing the capsule is bounded lowerly by a wall provided with holes for the free passage of said pointed rod and, respectively, for the passage of the air which is drawn into the chamber through said longitudinal hole, said wall which lowerly bounds the chamber being supported by the main body of the inhaler.

The structure and characteristics of the inhaler according to the invention will be more apparent from the ensuing description of one embodiment thereof given by way of non-limiting example with reference to the accompanying drawing in which:

FIG. 1 is a longitudinal section through the inhaler while housing a capsule which is in the process of being perforated by the needles carried by the movable part of the inhaler; and FIG. 2 is similar to FIG. 1 but shows the inhaler in the position which it assumes when the product in powder form is inhaled by the user.

DETAILED DESCRIPTION OF THE PREFERRED EMBODIMENTS

The inhaler shown in the figures comprises a main body, a movable part and a top part.

The main body is formed from a lower member 1 (with respect to the drawings), an intermediate profiled tubular jacket 2 securely fixed onto a tubular jacket 3 projecting from the lower member 1, and a transverse wall 4 rigid with the upper end of an appendix 5, along the periphery of which there are provided two or more holes 6 (which are rectilinear and parallel to the longitudinal axis of the jackets 2 and 3); two or more holes 7 are provided in the transverse wall 4 as can be seen from the drawings, but these holes are not strictly necessary.

On the upper free end of the jacket 2 there is fixed (for example by snap-fitting, screwing, or by a bayonet coupling system or the like) the top part 8, which is internally hollow and has its upwardly facing portion gradually decreasing with respect to that portion thereof which faces the jacket 2. Into the part 8 there extends a transverse wall 9 traversed by a plurality of small holes 10.

In the space defined by the cylindrical jacket 3 there is housed a substantially cylindrical body 11 which comprises the said holes 6 and from which a radial collar 12 projects. From the lower part (with respect to the drawings) of the body 11 there project two elongate appendices 13 which extend (and are axially translatable) through the apertures (not identified by numbers in the drawings) provided in the lower member 1. When in its rest state (FIG. 2), the collar 12 rests on the upper surface of the member 1, urged by a spring 14.

From the upper part of the body 11 there upwardly project the pointed ends of two needles or rods 15 which can translate through corresponding holes 16 (FIG. 2) provided in the discoidal part 4 (FIG. 1). When in the rest state (FIG. 2) the points of the needles are covered by the wall 4, whereas these needle points project above this wall (FIG. 1) and extend into a chamber 17 defined by the tubular jacket 2 and the top part 8 (when the movable part is pressed against the body 1–4 by overcoming the action of the spring 14), until they perforate the bottom of a capsule 18 housed in said chamber; when the thrust action exerted by a finger on the free end of the appendices 13 ceases and the spring 14 lowers the movable part until the collar 12 rests on the part 1 of the main body. Under these conditions the capsule 18 which now presents holes 19 at its lower end (FIG. 2) remains free to oscillate and to rotate within the inhaler chamber.

As can be seen from both figures, in the lower part of the chamber 17 there are provided a plurality of apertures 20 which open to the outside of the peripheral lateral surface of the tubular jacket 2, these apertures being all distributed about the periphery of the jacket 2 and being all inclined to the central axis of the chamber 17 in order to cause the capsule (by the effect of the inhalation) to rotate about its axis and at the same time to oscillate about the point at which the capsule rests on the wall 9. In addition, at the sides of the apertures 20 there project from the jacket 2 some inclined fins 21, the purpose of which is to prevent the fingers of the user which grip the inhaler from closing the apertures 20.

The structure of the aforedescribed inhaler is not explained in greater detail because it is substantially similar to that illustrated in U.S. Pat. No. 4,995,385 and EP-B-60388621. The main novelty of the inhaler of the invention is the presence of the holes 6 and 7 (the latter not indispensable) which, when the air is drawn in by the user through the inhaler mouthpiece (i.e. from the free end of the top part 8), enable the chamber 17 to receive at high velocity not only the air which passes through the apertures 20 (to cause lifting, rotation and shaking of the capsule 18), but in particular that air which passes through the holes 6 and possibly 7 (provided between the main body and the movable part, or in only one of these) and the holes 16 (provided in the transverse wall 4), the flow of this air being directed substantially from the bottom (with respect to the figures) upwards and acting such that the product in powder form is unable to deposit on the lower wall of the chamber 17 and partially block the holes 6.

In this manner the entire powder product leaving the capsule 18 is entrained upwards by the air stream drawn in and is inhaled by the user of the device.

It should be noted that the inhaler mouthpiece can be protected by a removable cover 22 or the like and that the free ends of the needles 15 can remain inserted into the holes 16 of the wall 4 (hence maintaining them closed) when the inhaler is in its rest state.

One embodiment of the inhaler has been described with reference to the drawings, however numerous constructional variations can be made thereto.

For example, the needles can consist of a single U-bent metal element, the loop or curved part of which is inserted into and retained by pressure in a seat provided in the upper end of the movable part. The transverse wall 4 can be replaced by a dome-shaped element with small holes for passage of air and of the opposing ends of the needles, it being inserted and retained by simple friction between the main body and the movable part. The holes for passage of air into the chamber below the capsule can be totally provided in the movable part, which would hence assume the form of a piston housed in and translatable within the cylindrical bore of the main body.

What is claimed is:

1. An inhaler for inhaling fine powder contained in capsules of substantially cylindrical shape, comprising an elongate main body, a top part applied to the upper end of the main body and defining therewith a chamber for housing a capsule containing a fine powder to be inhaled, and a movable part guided on the main body and having a portion which projects lowerly from the main body and a portion which has at least one pointed rod extending towards said chamber, the movable part being translatable between an inactive position in which the pointed end of the rod is outside said chamber and an active position in which said end of the rod extends into the chamber in order to perforate a capsule housed therein, in the lower part of the chamber there being provided a plurality of apertures which open to the outside of the peripheral lateral surface of the inhaler, the upper part of the chamber being bounded by a wall which is traversed by a plurality of small holes and is rigid with the top part, the dimensions of the chamber being greater than those of the capsule which it is intended to house, wherein the movable part comprises at least one longitudinal hole positioned to provide air to the lower part of said chamber from the vicinity of the lower portion of the movable part to minimize deposition of the fine powder on the lower part of the chamber during inhalation.

2. An inhaler as claimed in claim 1, wherein said at least one longitudinal hole is rectilinear and is parallel to the axis of translation of the movable part.

3. An inhaler as claimed in claim 2, wherein between the main body and the movable part there acts at least one spring which urges the movable part towards its inactive position.

4. An inhaler as claimed in claim 3, wherein the chamber for housing the capsule is bounded lowerly by a wall provided with at least one hole for the free passage of said at least one pointed rod and the air which is drawn into the chamber through said at least one longitudinal hole, said wall which lowerly bounds the chamber being supported by the main body of the inhaler.

5. An inhaler as claimed in claim 4, wherein said at least one hole comprises a plurality of holes.

* * * * *